United States Patent [19]
Garrison

[11] Patent Number: 6,074,210
[45] Date of Patent: Jun. 13, 2000

[54] DENTAL WEDGE FOR UTILIZATION IN DENTAL RESTORATION

[76] Inventor: John E. Garrison, 110 E. DeWitte La., Spring Lake, Mich. 49456

[21] Appl. No.: 09/141,226

[22] Filed: Aug. 27, 1998

Related U.S. Application Data

[63] Continuation of application No. PCT/US98/14701, Jul. 13, 1998.
[60] Provisional application No. 60/057,712, Aug. 27, 1997.

[51] Int. Cl.[7] .................................................. A61C 7/00
[52] U.S. Cl. ............................................................ 433/149
[58] Field of Search ............................................. 433/149

[56] References Cited

U.S. PATENT DOCUMENTS

| | | | |
|---|---|---|---|
| 3,193,094 | 7/1965 | Schulstad | 433/149 |
| 3,815,243 | 6/1974 | Eames | 433/149 |
| 3,890,714 | 6/1975 | Gores | 433/149 |
| 4,468,199 | 8/1984 | Weikel | 433/149 |

*Primary Examiner*—John J. Wilson
*Attorney, Agent, or Firm*—Rader, Fishman & Grauer PLLC

[57] ABSTRACT

The dental wedge includes a generally tetrahedral body having a central longitudinal apex flanked by a pair of resilient side walls, connecting a narrow distal point and a wider proximal end, and having an open underside opposite thereto, as well as a protuberance extending axially from the proximal end and adapted for gripping by a dental implement.

22 Claims, 3 Drawing Sheets

DENTAL WEDGE FOR UTILIZATION IN DENTAL RESTORATION

CROSS-REFERENCE TO RELATED APPLICATIONS

This application is a continuation of PCT/US98/14701, filed Jul. 13, 1998, which claims the benefit of U.S. Provisional Application No. 60/057,712 filed on Aug. 27, 1997.

BACKGROUND OF THE INVENTION

1. Field of the Invention

The present invention relates generally to the field of dental instruments and more particularly to dental wedges.

2. Related Art

Dental wedges are well known in the art and have been used in restorative dentistry for over a century. Generally, dental wedges are used to separate the teeth and hold a matrix band against the side of the tooth being restored or repaired. These functions are important for the successful restoration of the form and function of teeth. Unless adequate separation of the teeth is achieved, the adjacent teeth, once restored, will inadequately contact one another. Without adequate contact between the teeth, food will pack and otherwise accumulate in between the teeth, leading to decay and periodontal problems. Moreover, unless the matrix band conforms adequately to the side of the tooth, filling material can be forced below the gum line or leave the tooth with unnatural and irregular contours known as ledges, overhangs, and underhangs. These flaws aid and cause plaque accumulation, leading to decay and periodontal problems.

To prevent these problems, the dentist uses a wedge, which is typically piece of wood or plastic of a basic tetrahedral shape, thus tapered to a point on one end. In use, a wedge is inserted into the space between the adjacent teeth at the gum line and forced into the space to cause separation of the teeth so that they may be restored. This causes the matrix band material to be pressed against the gingival portion of the tooth at the floor of a preparation, thereby closing the space and preventing the overhang.

The ideal dental wedge should be relatively hard in order to drive the teeth apart at least the thickness of the average matrix band (approximately 0.002 inch). When the wedge and matrix band are removed, the restored teeth should rebound to their normal physiological position due to the elastic memory of the periodontal membrane and maintain physiologic contact in order to prevent food debris from packing between the teeth during chewing. The wedge should also provide resistance against the matrix band so as to prevent deformation or dislodgment due to the outward pressure a dentist typically exerts when packing restorative materials in the matrix-confined cavity space.

Most commercially available dental wedges are a basic tetrahedral shape and made of various types of wood. To accommodate different sizes of interproximal spaces, wedges are generally available in various sizes from small to large and the size used is determined by the size of the interproximal space. While these wedges are hard enough to allow the teeth to be driven apart, they suffer from the problem of not conforming adequately to the interproximal surface of the tooth.

Another basic requirement of a dental wedge is that it be able to cause the matrix band to intimately conform to the anatomical surfaces of the tooth to be restored. Often, the interproximal surface of the tooth will be concave. Wherever a dental wedge does not intimately contact the flexible matrix band and force it against the concave surface of the tooth, the band is unsupported. In such a condition, a gap or opening will develop in response to the pressure of packing the restorative material into the matrix-confined cavity preparation. These gaps allow the filling material to push past the matrix and create a ledge, overhang, or an otherwise unacceptable contour of the tooth in the interproximal space. Further, the gaps allow blood and other fluids to enter the band, thereby contaminating the restorative materials, which results in a compromised restoration as explained below. Rigid, fixed-shaped wedges or wedge type devices known in the art do not adapt well to the variable contours of the interproximal spaces.

A further problem of the present art is that the insertion of the rigid wedge is detrimental to the interproximal gingival tissues. Gingival tissue is soft and displaceable. Thus, a rigid wedge design does not accommodate the gingival tissue and simply and traumatically displaces the tissue, resulting in upward force on the teeth walls. Tearing the gingival tissue permits blood, saliva, and other contaminants to flow into the preparation cavity. Because dental restorative materials only function optimally when dry, the service and longevity of the restoration are compromised.

The dental wedge must also be easily removed from the interproximal space between the teeth. While a wedge that resists backing out is a desired characteristic of wedges, such a characteristic makes the wedge more difficult to remove from between the teeth. To accommodate placement and removal, a wedge may include a small protuberance which is adapted to be grasped by an implement such as pliers, as seen in U.S. Pat. No. 4,696,646. Easy placement and removal further reduces trauma to the gingival tissue, which results in a cleaner and drier work surface. Further, a flexible wedge that forces the band against the concavities of the interproximal tooth seals the preparation cavity against fluid seepage due to any incidental trauma that might occur.

Numerous attempts have been made to accommodate the varying interproximal surfaces of teeth, while avoiding trauma to the soft tissues and maintaining adequate stiffness to remain in place. Most dental wedges, however, share the common problem that they adhere to the basic tetrahedral shape, which on the inferior surface of the tetrahedron typically causes trauma to the gingival tissues upon surface. The wedge described in U.S. Pat. No. 3,890,714, however, includes less surface area on the side of the wedge communicating with the gingival tissue. This wedge suffers from three problems. First, the wedge body is substantially hollow, which results in ineffectual strength for conforming a matrix band to any tooth defects and insufficient strength to place the wedge and to separate the teeth. Second, the wedge does not include a protuberance for grasping the wedge with dental pliers or the like, which makes removal of the wedge particularly difficult. Third, the wedge has a tendency to back out of the interproximal space, thereby interrupting the dentist who must re-insert the wedge.

SUMMARY OF THE INVENTION

The present invention provides a one-piece dental wedge which is capable of separating adjacent teeth and conforming a matrix band to the irregular surfaces of the tooth being restored, and doing so with minimal compression of gingival tissue between the teeth. This dental wedge possesses elastic properties which enable it not only to recover deformation but also rebound to the irregular contours of the tooth being repaired. The elasticity enables the wedge to be forced between two teeth and then expand into a concave, interproximal surface in one of the teeth with enough force to cause a matrix band to adapt to the interproximal contours.

The present wedge comprises a one-piece substantially tetrahedral body having a small protuberance on its blunt end adapted to be grasped by a dentist's implement for accommodating placement and removal of the wedge. In an aspect of the invention, a tapering V-shaped interior cut out from the side of the tetrahedron in communication with the gingival tissue. Preferably made from plastic, the wedge is firm enough to provide resistance to compression when wedged between two teeth, and also capable of rebounding from compression to conform to the contours of two surfaces.

An alternative embodiment of the present wedge according to the invention is similar to the wedge described above but includes a series of serrations formed on the outer surface, as well as a bottom surface rear portion angled upwardly generally parallel to the top surface from approximately a mid point of the bottom surface of the wedge to the proximal end portion, which includes the small protuberance adapted to be grasped by a dentist's implement. The series of serrations provide traction for the wedge when it is inserted between adjacent teeth to prevent the wedge from backing out of the interproximal space. Further, the wedge includes a rounded distal leading point for a wider body without unnecessary length, as well as for promoting safe insertion of the wedge between the adjacent teeth.

Other objects, features, and advantages of the invention will be apparent from the ensuing description in conjunction with the accompanying drawings.

BRIEF DESCRIPTION OF THE DRAWINGS

In the drawings.

The invention will now be described with reference to the drawings in which.

DETAILED DESCRIPTION

Figure 1:
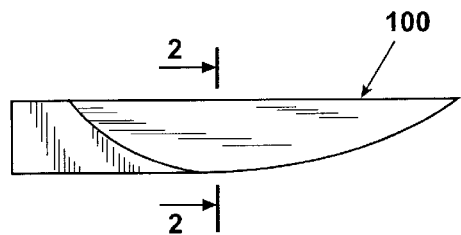
FIG. 1 is a side elevational view of the wedge according to the prior art.
Figure 2:
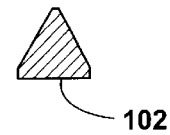
FIG. 2 is cross sectional view taken along line 2—2 of FIG. 1.
Figure 3:
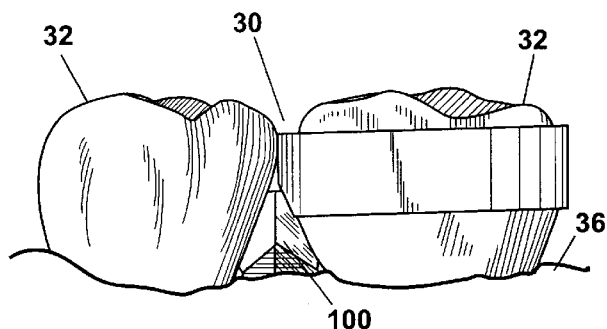
FIG. 3 is a front elevational view of the wedge of FIG. 1.
Figure 5:
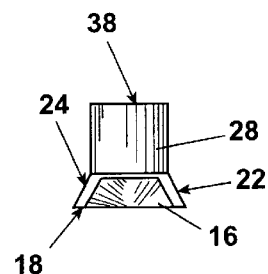
FIG. 5 is an end elevational view of the wedge of FIG. 4.
Figure 4:
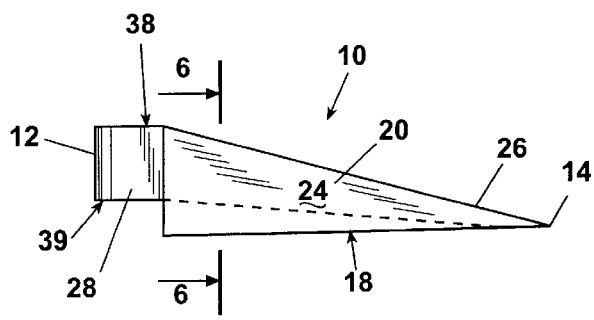
FIG. 4 is a side elevational view of a wedge according the invention.
Figure 6:
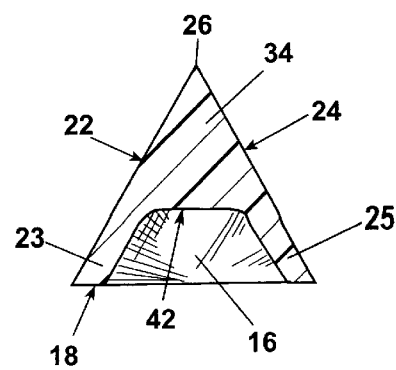
FIG. 6 is a cross sectional view taken along line 6—6 of FIG. 4.

A dental wedge 100 of the prior art is illustrated in FIGS. 1–3. The wedge 100 has an overall tetrahedral shape including a substantially flat lower surface 102 which is prone to cause trauma to the gingival tissue 36 upon insertion between two teeth 32. A dental wedge 10 of the present invention is shown in FIGS. 4–9. Looking first at FIGS. 4–7, it can be seen that the wedge 10 includes a body 20, which tapers overall from a proximal end portion 12 to a distal leading point 14.

Figure 8:
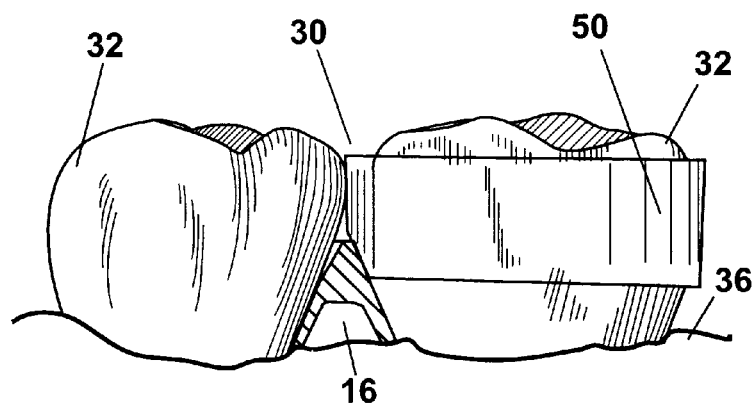
FIG. 8 is a cross section of the wedge similar to FIG. 6, in use between two teeth.
Figure 9:
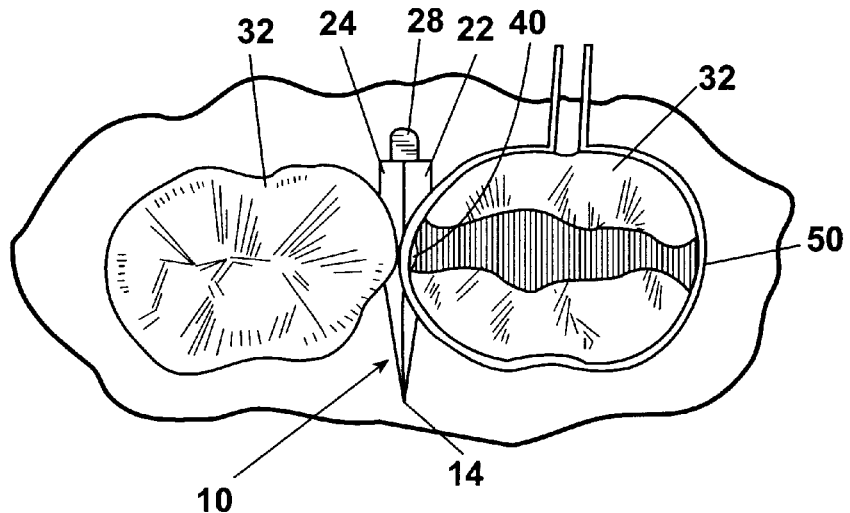
FIG. 9 is a top plan view of the wedge of FIG. 4 in use between two teeth.

As illustrated by FIGS. 8 and 9, the wedge 10 is positioned within an interproximal space 30 between teeth 32 and superior to the gingival tissue 36. As shown in FIG. 9, the teeth 32 include a concave defect 40, which is a typical depressed surface on the sides of the teeth 32 facing the interproximal space.

Figure 7:
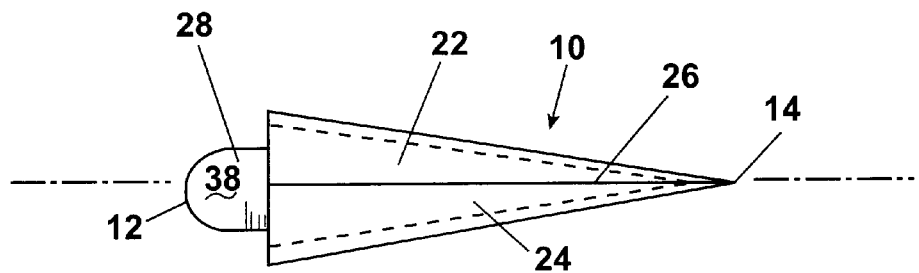
FIG. 7 is a top plan view of the wedge of FIG. 4.

The body has a longitudinal apex 26 about which it is symmetrical in plan view, as illustrated in FIG. 7. Looking also at FIGS. 4–6 again, the wedge 10 has a generally elongated tetrahedral shape, including an inferior face 18 and two symmetrical side faces 22 and 24. The side faces 22, 24 are triangular and planar. The inferior face 18, on the other hand, has a shallow recess 16, which tapers from its greatest depth at the end portion 12 to the leading point 14. Thus, a lower portion of the side faces 22, 24 form relatively thin walls 23, 25 which bound the shallow recess 16. The walls 23, 25 are structurally thin enough to flex in response to pressures exerted by adjacent teeth 32, to conform to any irregular shape on the teeth 32, and to rebound upon relief from such pressure as in a concavity on an adjacent tooth. Further, the walls' resiliency is strengthened by a solid body portion 34 extending between the apex 26 and a concave face 42 partially defining the shallow recess 16.

The end portion 12 of the wedge 10 includes a protuberance 28, adapted for engagement by a suitable implement for easy placement of the dental wedge into the interproximal space 30 between teeth 32. The protuberance 28 comprises a flat upper surface 38 and a corresponding flat lower surface 39.

Figure 10:
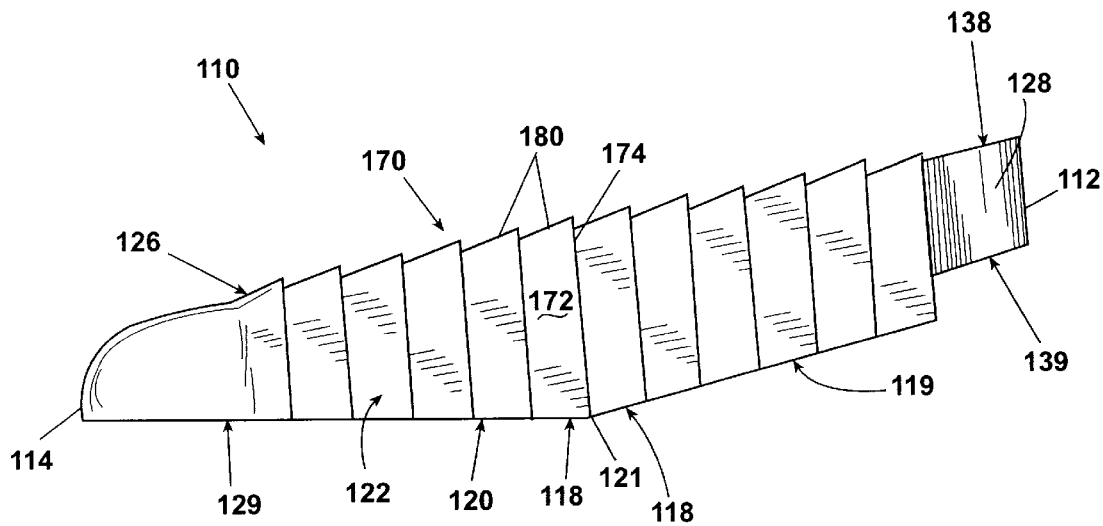
FIG. 10 is a side elevational view of a wedge according to a further embodiment of the invention.
Figure 11:
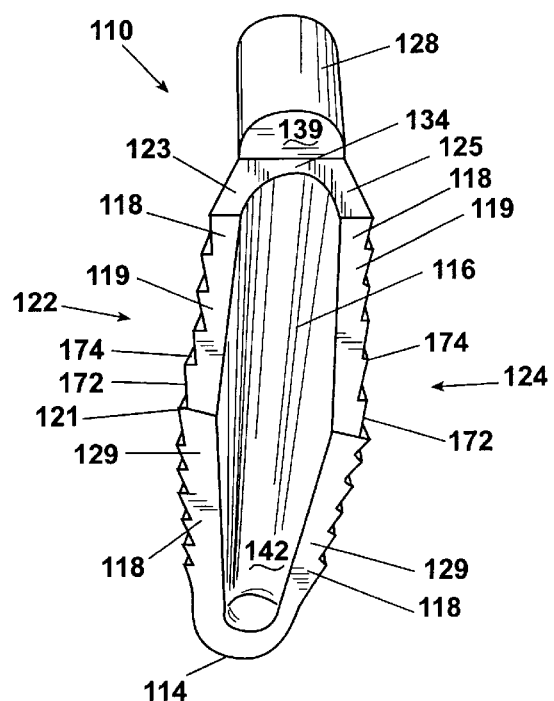
FIG. 11 is a bottom elevational view of the wedge of FIG. 10.

As illustrated by FIGS. 10 and 11, a further embodiment of a dental wedge, according to the invention is shown. As shown in FIG. 10, a dental wedge 110 includes a body 120 that tapers overall from a proximal end portion 112 to a distal leading point 114.

The body 120 has a longitudinal axis of symmetry in plan view. Further, the wedge 110 has a generally elongated tetrahedral shape, including a lower face 118 and two symmetrical side faces 122, 124. A lateral cross-section of the body 120 is generally triangular, and the lower face 118 has a shallow recess 116 that tapers from its greatest depth at the proximal end portion 112 to the leading point 114. Thus, a lower portion of the side faces 122, 124 form relatively thin walls 123, 125 that bound the shallow recess 116. Preferably, the walls 123, 125 are structurally thin enough to flex in response to pressures exerted by adjacent teeth 32, whereby they are adapted to conform to any irregular shape on the teeth 32, and rebound upon relief from such pressure as in a concavity on an adjacent tooth. Further, the walls' resiliency is strengthened by a solid back portion 134 extending between the apex 126 and a concave face 142 partially defining the shallow recess 116.

The end portion 112 of the wedge 110 includes a protuberance 128, which is adapted for engagement by a suitable implement for easy placement of the dental wedge 110 into an interproximal space 30 between adjacent teeth 32. The protuberance 128 comprises preferably a flat upper surface 138 and a corresponding flat lower surface 139. The leading point 114 is preferably rounded, whereby it is safer for insertion within an interproximal space with a lower risk of gingival trauma than a sharp point as shown in the prior embodiment.

The side faces 122, 124 defining the body 120 have a textured outer surface 170 to prevent backing out of the wedge 110 from the interproximal space 30, preferably formed of a series of angled serrations 180, which define an outer surface notched with tooth-like projections. Alternatively, the textured outer surface may be knurled or rippled. The angled serrations 180, each of which provides a ramped surface 172 adapted to ease insertion of the wedge 110 and an edge 174 at the end of each ramped surface 172 to resist removal of the wedge, are specifically adapted to resist backing out once placed within the interproximal space 30. By the inclusion of the protuberance 128, however, wedge 110 is simply removable by a suitable dental implement. Thus, the textured outer surface 170 provides traction for resisting inadvertent outward movement of the wedge 110 from the interproximal space, which aids the wedge in providing adherence of the matrix band 50 to the defects of the teeth 32.

The lower portion of the side faces 122, 124 on the lower face 118 include a rearward portion 119 that extends rearwardly from an intermediate portion 121 toward the end portion 112 at an angle relative to a forward portion 129 that extends forwardly from the intermediate portion 121 toward the distal leading point 114. The intermediate portion 121 may be a point, but preferably represents a zone of engagement where a minimal portion of the lower edge 118 is presented to the gingival tissues when the wedge is inserted between the teeth.

It is important to note that for each of the two embodiments described above, the combination of certain features according to the invention are not unique to one embodiment or the other. For example, the first embodiment might include serrations but not an angled lower surface; or, the second embodiment might include an angled lower surface but no serrations. Thus, the features described with reference to a particular embodiment may be incorporated into the other embodiments, in whole or in part, as should be well understood by one of skill in the art.

Preferably, the wedge 10 is made of a polymer plastic. However, it is entirely within the scope of the present invention to form the wedge from many other types of materials, such as synthetics, other plastics, or wood. The only requisite is that there be sufficient resilience to permit flexure of the walls 23, 25.

Use of the dental wedge is best shown in FIGS. 8 and 9. While the wedge 10 is shown, FIGS. 8 and 9 apply equally well to the wedge 110, as does the following description. The wedge 10 is first placed between adjacent teeth 32, with the leading point 14 inserted first, and positioned to provide adequate separation between the teeth 32. Using pressure from a dental implement (not shown) on the protuberance 28, the wedge 10 is inserted between two teeth 32 until resistance is felt.

As is well known, separation between the teeth 32 is necessary to compensate for the thickness of a matrix band 50 used in restorative dentistry. The matrix band 50 is placed around a tooth 32 and a dental wedge 10 is inserted between the tooth 32 and the adjacent tooth 32 to separate the teeth 32 and conform and hold the matrix band 50 against the tooth 32 to be restored. When the wedge 10 is inserted, the walls 23, 25 flex into the groove 16 as the faces 22, 24 engage the matrix band 50 surrounding the teeth 32. When the faces 22, 24 meet a concave irregularity on the tooth 32, the walls 23, 25 carrying the faces at a lower portion of the wedge rebound and conform the matrix band 50 to the irregularity.

To remove the wedge 10 from the interproximal space 30, a dental implement (not shown) will simply grasp the protuberance 28, clamping into it at the upper and lower surfaces 38, 39, and pull the wedge 10 from between the teeth 32. The teeth 32 will rebound to their normal physiological position due to the elastic memory of the periodontal membrane and maintain physiologic contact with adjacent teeth 32 in order to prevent food debris from packing between the teeth during chewing.

Reasonable variation and modification are possible within the spirit of the foregoing specification and drawings without departing from the scope of the invention.

What is claimed is:

1. A dental wedge comprising:

a generally elongated tetrahedral body having a central longitudinal apex flanked by a pair of resilient side walls, connecting a distal point and a proximal end, and having an open underside opposite the apex defining a shallow recess;

each resilient side wall having a lower edge comprising a forward portion extending from the distal point to an intermediate portion and a rearward portion extending from the proximal end to the intermediate portion, said forward and rearward portions being at an angle relative to each other, wherein the intermediate portion presents a limited surface area of the underside for contact with gingival tissue during insertion and removal of the dental wedge; and a protuberance extending axially from the proximal end and adapted for gripping by a dental implement.

2. A dental wedge according to claim 1 wherein a solid body portion extends between the apex and the lower edge of the resilient sidewalls partially defining the open underside.

3. A dental wedge according to claim 2 wherein the solid body portion includes a concave face partially defining the shallow recess.

4. A dental wedge according to claim 2 wherein the protuberance extends axially from the solid body portion.

5. A dental wedge according to claim 1 wherein the distal point includes a rounded leading edge, thereby lessening the risk of gingival trauma upon insertion of the wedge between adjacent teeth.

6. A dental wedge according to claim 1 wherein the resilient side walls include a textured outer surface, thereby providing increased traction for the wedge on adjacent teeth.

7. A dental wedge according to claim 6 wherein the textured outer surface includes a series of serrations.

8. A dental wedge according to claim 7 wherein the series of serrations includes between 8 and 15 serrations.

9. A dental wedge according to claim 7 wherein the serrations are angled.

10. A dental wedge according to claim 6 wherein the textured outer surface includes knurling.

11. A dental wedge according to claim 6 wherein the textured outer surface includes a series of ripples.

12. A dental wedge according to claim 1 wherein the intermediate portion is generally further from the central longitudinal apex than the forward and rearward portions to define a zone of engagement with gingival tissues.

13. A dental wedge comprising:

a generally elongated tetrahedral body having a central longitudinal apex flanked by a pair of resilient side walls, connecting a distal point and a proximal end, and having an open underside opposite the apex;

each resilient side wall having a lower edge comprising a forward portion extending from the distal point to an intermediate portion and a rearward portion extending from the proximal end to the intermediate portion, said forward and rearward portions being at an angle relative to each other, wherein the intermediate portion presents a limited surface area of the underside for contact with gingival tissue during insertion and removal of the dental wedge;

a solid body portion extending approximately midway between the apex and the lower edge of the resilient side walls partially defining the open underside; and a concave face of the solid body portion partially defining the open underside.

14. A dental wedge according to claim 13 wherein a protuberance extends axially from the proximal end and is adapted for gripping by a dental implement.

15. A dental wedge according to claim 14 wherein the protuberance extends axially from the solid body portion.

16. A dental wedge according to claim 13 wherein the narrow distal point includes a rounded leading edge, thereby lessening the gingival trauma upon insertion of the wedge between adjacent teeth.

17. A dental wedge according to claim 13 wherein the resilient side walls include a textured outer surface, thereby providing increased traction for the wedge on adjacent teeth.

18. A dental wedge according to claim 17 wherein the textured outer surface includes a series of serrations.

19. A dental wedge according to claim 18 wherein the series of serrations includes between 8 and 15 serrations.

20. A dental wedge according to claim 18 wherein the serrations are angled.

21. A dental wedge according to claim 17 wherein the textured outer surface includes knurling.

22. A dental wedge according to claim 17 wherein the textured outer surface includes a series of ripples.

* * * * *

UNITED STATES PATENT AND TRADEMARK OFFICE
CERTIFICATE OF CORRECTION

PATENT NO.  : 6,074,210
DATED       : June 13, 2000
INVENTOR(S) : John E. Garrison It is certified that error appears in the above-identified patent and that said Letters Patent is hereby corrected as shown below:

Column 7,
Line 18, "narrow" should be omitted.

Signed and Sealed this

Seventh Day of August, 2001

*Attest:*

NICHOLAS P. GODICI
*Attesting Officer*     *Acting Director of the United States Patent and Trademark Office*